(12) United States Patent
Barak

(10) Patent No.: US 6,182,698 B1
(45) Date of Patent: *Feb. 6, 2001

(54) VALVE ASSEMBLY

(75) Inventor: Swi Barak, Caesarea (IL)

(73) Assignee: Societe des Produits Nestle SA, Vevey (CH)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/930,073

(22) PCT Filed: Jun. 7, 1996

(86) PCT No.: PCT/IB96/01007

§ 371 Date: Apr. 13, 1998

§ 102(e) Date: Apr. 13, 1998

(87) PCT Pub. No.: WO97/00399

PCT Pub. Date: Jan. 3, 1997

(30) Foreign Application Priority Data

Jun. 16, 1995 (IL) .......................................... 114190

(51) Int. Cl.⁷ .......................... A61M 37/00; A61M 39/26; F16K 15/14
(52) U.S. Cl. ........................... 137/845; 137/512; 604/83; 604/247
(58) Field of Search .................................. 137/845, 849, 137/854, 512; 251/149.1; 604/256, 247, 80, 82, 83; 417/566

(56) References Cited

U.S. PATENT DOCUMENTS

| | | | |
|---|---|---|---|
| 2,908,283 | 10/1959 | Kiffer et al. | 137/845 X |
| 3,119,411 * | 1/1964 | Bock et al. | 137/512 X |
| 3,485,419 * | 12/1969 | Taylor | 417/566 X |
| 3,496,874 * | 2/1970 | Findlay | 137/859 X |
| 3,599,657 * | 8/1971 | Maldavs | 137/512 X |
| 3,601,151 | 8/1971 | Winnard | 137/846 |
| 3,710,942 | 1/1973 | Rosenberg | 137/854 X |
| 4,003,398 | 1/1977 | Duveau | 137/845 X |
| 4,100,930 | 7/1978 | Orcutt | 137/68.26 |
| 4,246,932 * | 1/1981 | Raines | 137/512 |
| 4,583,981 | 4/1986 | Urquhart et al. | 604/80 |
| 4,666,429 | 5/1987 | Stone | 604/83 |
| 4,729,401 * | 3/1988 | Raines | 137/512 |
| 4,830,052 | 5/1989 | Oberlin et al. | 137/68.24 |
| 4,915,688 | 4/1990 | Bischof et al. | 604/83 |
| 5,037,390 | 8/1991 | Raines et al. | 604/83 |
| 5,230,706 | 7/1993 | Duquette | 604/83 |
| 5,269,771 | 12/1993 | Thomas et al. | 251/149.1 X |
| 5,273,546 | 12/1993 | McLaughlin et al. | 137/849 X |
| 5,279,557 | 1/1994 | Lomick | 604/80 |

* cited by examiner

Primary Examiner—John Rivell
(74) Attorney, Agent, or Firm—Bell, Boyd & Lloyd LLC

(57) ABSTRACT

The valve assembly has inlet and outlet members with valve elements disposed between the two members. The valve is a resilient membrane having one or more through holes. When there is no pressure differential across the valve, the hole walls in the membrane collapse inwards closing off the valve against liquid flow. At or above a threshold pressure differential across the valve, the membrane is stretched which opens up the hole or holes to allow the passage of liquid.

3 Claims, 5 Drawing Sheets

US 6,182,698 B1

VALVE ASSEMBLY

BACKGROUND OF THE INVENTION

The present invention relates to valve assemblies for liquid transfer.

SUMMARY OF THE INVENTION

In accordance with the invention there is provided a valve assembly for liquid transfer, comprising a liquid inlet, a liquid outlet and a valve member disposed between the inlet and outlet; the valve member comprising a resilient membrane separating between the inlet and the outlet, the membrane having one or more holes; in a state where there is no pressure difference between the membrane's two sides, the walls of the one or more holes are collapsed and no liquid can pass therethrough, and in a certain threshold level, the stretching of the membrane causes opening of the one or more holes to allow liquid to pass from one side of the membrane to the other.

In accordance with an embodiment of the invention, the valve is of the one-way type allowing fluid transfer only in one direction.

In accordance with another embodiment of the invention, the valve assembly comprises an auxiliary member whereby the membrane can be stretched manually to bring to opening of the one or more holes.

The pressure threshold is determined by the thickness and surface area of the resilient member and the size of said one or more holes.

By still another embodiment of the invention, the valve assembly comprises a piercing member for piercing the membrane so as to create at least one hole therein, the at least one hole being of the kind defined above.

By another aspect of the present invention there is provided a fluid valve assembly consisting of a first valve assembly and a second valve assembly, each of the first and second valve assemblies being independently selected from the group consisting of a valve assembly according to any one of the proceeding claims, wherein a liquid outlet of said second valve assembly is in flow communication with a liquid inlet of said first valve assembly.

The invention will now be illustrated in the following non-limiting specific embodiments with particular reference to the annexed drawings.

DETAILED DESCRIPTION OF THE PREFERRED EMBODIMENTS

Figure 1:
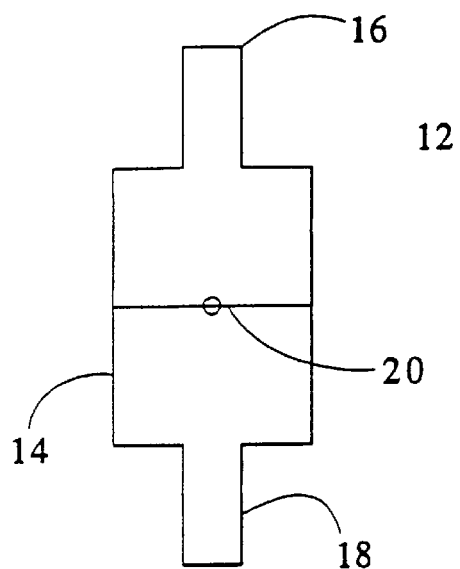
FIG. 1 shows a schematic representation, in longitudinal cross-section, through a valve assembly in accordance with the invention.
Figure 2:
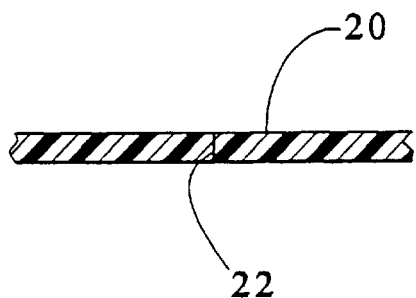
FIG. 2 is an enlargement of the circled area in FIG. 1.
Figure 3:
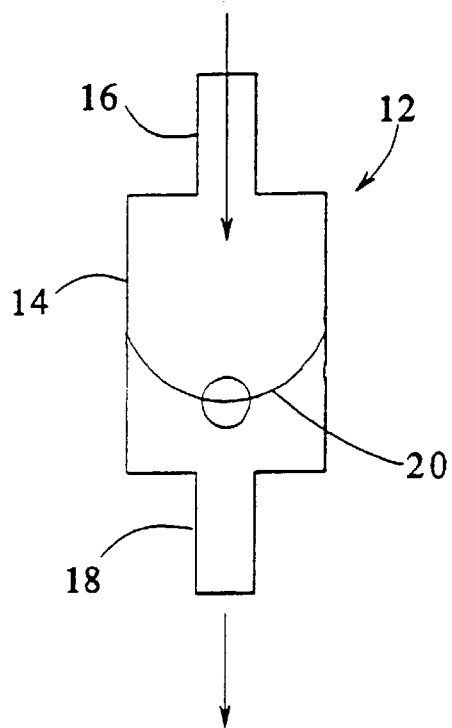
FIG. 3 shows the valve assembly of FIG. 1 under the application of pressure.

Reference is first being made to FIGS. 1–4 giving a schematic representation of a valve assembly in accordance with the invention. The valve assembly 12 comprises a body 14 having a liquid inlet 16 and liquid outlet 18. (The use of the terms "outlet" and "inlet" in connection with this embodiment is in fact only for convenience as can be appreciated. The valve here is symmetrical and the roles of inlet and outlet can be reversed). Disposed between inlet 16 and outlet 18 and separating the two is a resilient membrane 20, made for example of silicone rubber. As can be seen in FIG. 2, there is a hole 22 within membrane 20 which is in a position where there is a hole 22 within membrane 20 which is in a position where there is no pressure difference between the two sides of the membrane, the walls thereof are collapsed and the hole is totally closed.

Figure 4:
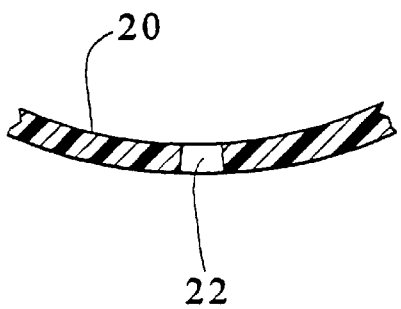
FIG. 4 is an enlargement of the circled area in FIG. 3.

When liquid pressure is applied through inlet 16 (represented schematically by the arrow in FIG. 3), the membrane 20 deforms and stretches and consequently the opening expands, forming an open hole allowing fluid flow, as can be seen in FIG. 4.

Figure 5:
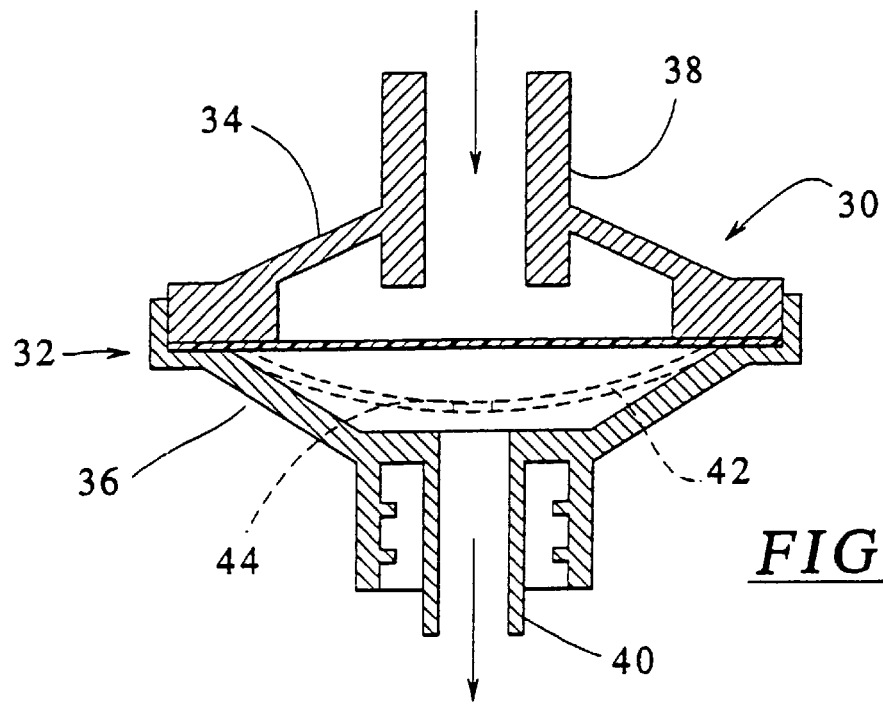
FIG. 5 is a longitudinal cross-section of a valve assembly in accordance with an embodiment of the invention in which fluid can be transferred in both directions.

Reference is now being made to FIG. 5 showing a valve assembly 30 in accordance with an embodiment of the invention. The valve assembly comprises housing 32 consisting of two members 34 and 36 engaged with one another. Member 34 defines a fluid inlet 38 and member 36 defines a fluid outlet 40, which is in this case is a luer-type connector. Membrane 42 is disposed between the inlet and the outlet and held in place by juxtaposed portions of members 34 and 36.

Membrane 42 has a hole which, in the rest position shown in FIG. 5 is closed. When liquid pressure is applied the membrane is deformed (represented by the dotted lines), hole 44 opens allowing fluid flow. Similarly as in the case of the valve assembly of FIG. 1–4, liquid can in principle flow in either direction, depending on the direction of applied fluid (here again, components 38 and 40 are defined as "inlet" and "outlet", respectively, for the sake of convenience, although the flow direction from inlet 38 to outlet 40 is the preferred direction).

Figure 6:
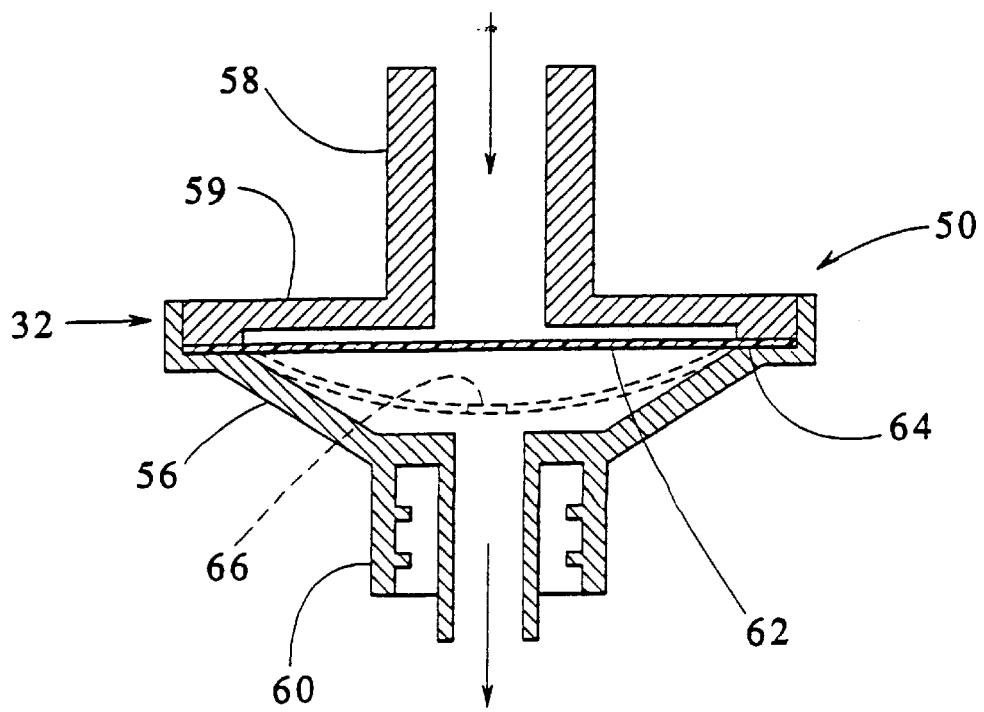
FIG. 6 is a longitudinal cross-section through a valve in accordance with another embodiment of the invention in which fluid can be transferred only in one direction.

Reference is now being made to FIG. 6 showing the valve assembly 50 in accordance with another embodiment of the invention in which liquid flow is permitted only in one direction. The valve assembly 50 comprises a housing 52 consisting of a first member 54 and a second member 56 defining respective inlet 58 and outlet 60, the latter being a luer-type connector. Disposed within casing 52, and held between juxtaposed portions of members 54 and 56, is a resilient membrane 62. As can be seen, member 54 has a wall portion 64 which lies parallel to the membrane 62 and consequently the membrane can be deformed only in the opposite direction to wall portion 64 (towards outlet 60). When liquid pressure applied from inlet 58 (represented by the arrow) exceeds a certain threshold, the membrane deforms (the deformed member being represented by a dotted line) and a pre-existing hole in the membrane 66 which opens up, allows then fluid flow between inlet 58 and outlet 60.

Figure 7:
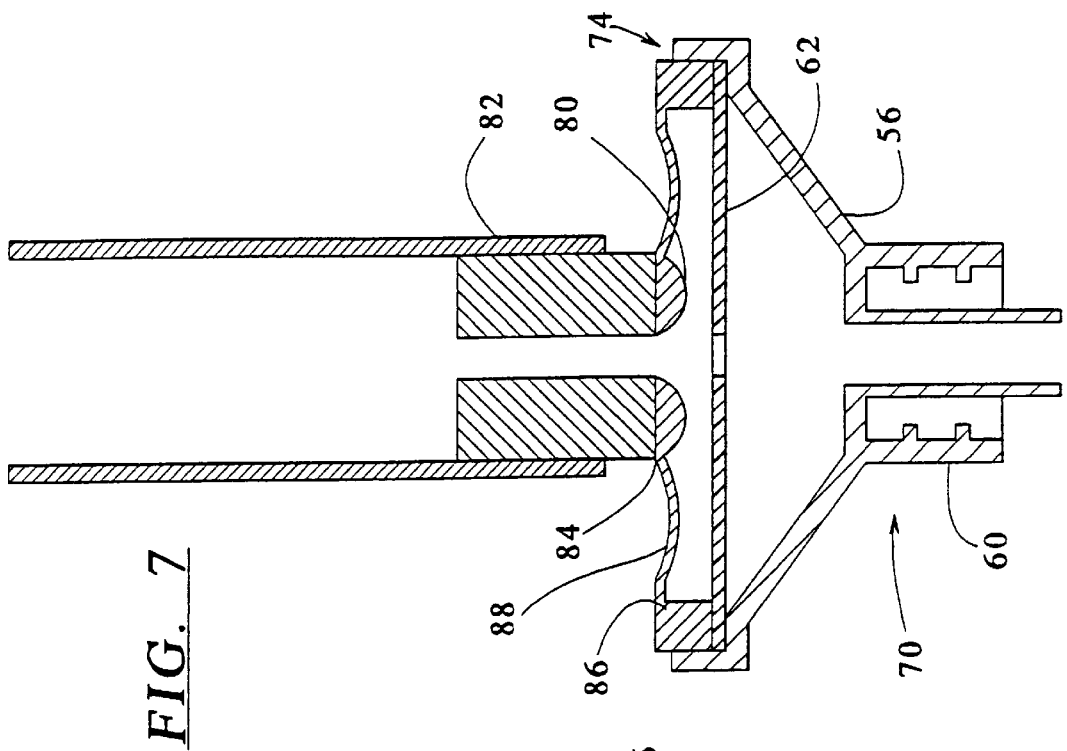
FIG. 7 is a longitudinal cross-section through a valve in accordance with another embodiment of the invention, comprising means which allow a manual distortion of the membrane to allow stretching and opening of the holes.
Figure 8:
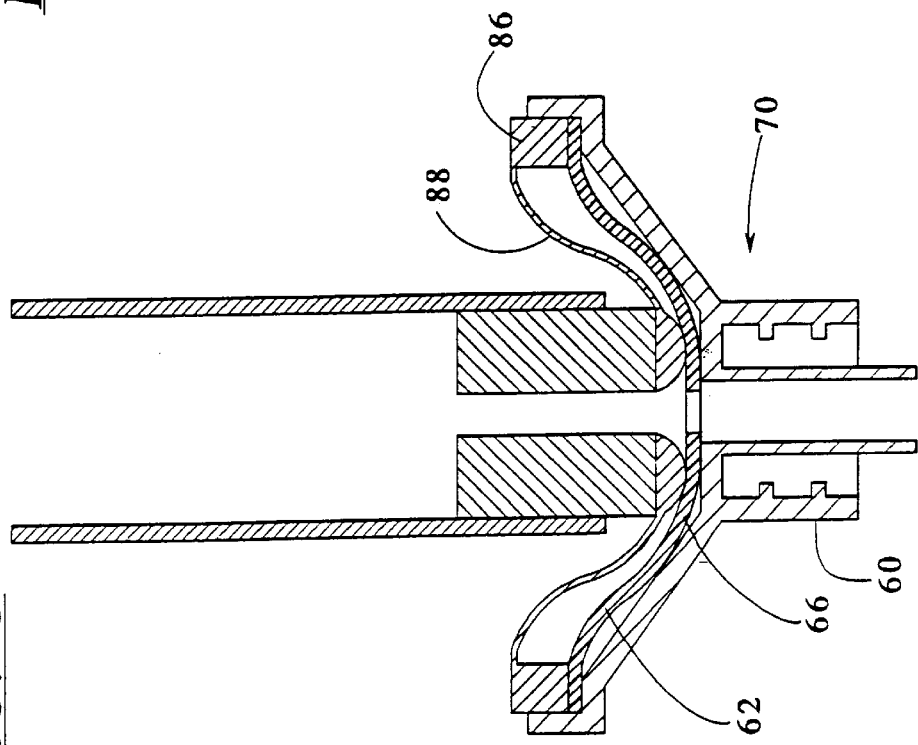
FIG. 8 is a longitudinal cross-section through a valve assembly of FIG. 7 after application of the manual force.

Reference is now being made to FIGS. 7 and 8 which show a valve assembly 70 in accordance with another embodiment. The difference between this embodiment and the embodiment shown in FIG. 6 resides in first member 74 and all other members, which are given the same reference numerals as in FIG. 6, perform in fact the same function. Member 74 has a central portion 80 defining an inlet 82 and an annular bulge 84 which lies proximal to membrane 62. Central portion 80 is linked to the periphery 86 of member 74 by means of an intermediary flexible shoulder portion 88 which allows relative axial movement between central portion 82 and the periphery 86.

When the central portion is moved versus the periphery so that it presses upon membrane 62, as can be seen in FIG. 8, the membrane deforms and hole 66 opens and permits liquid flow, the assembly of this embodiment operates essentially in the same manner as that of FIG. 6, i.e. it permits only unidirectional liquid flow.

Figure 9:
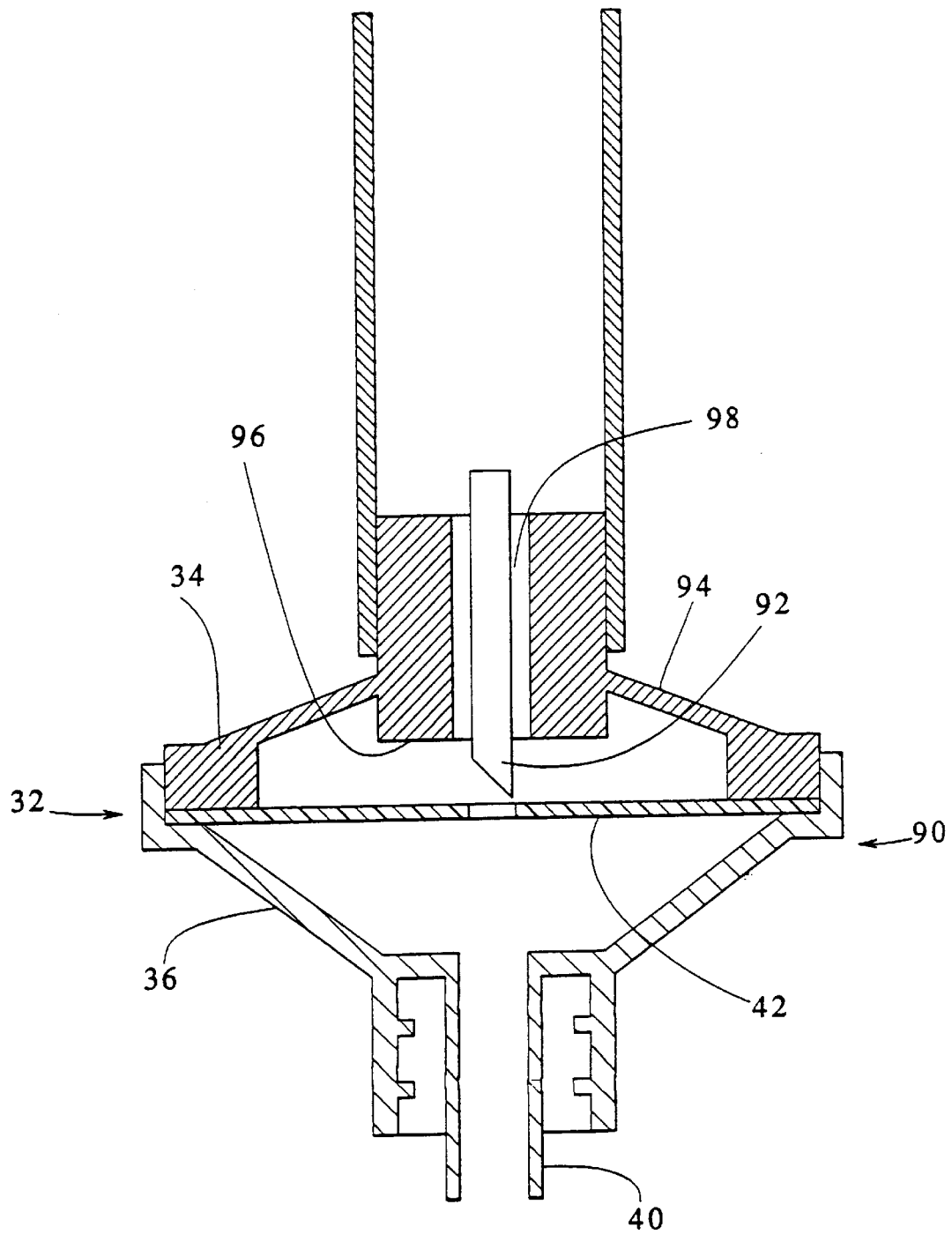
FIG. 9 is a longitudinal cross-section through a valve assembly in accordance with another embodiment of the invention comprising a piercing membrane.

Reference is now being made to FIG. 9 which shows a valve assembly 90 in accordance with another embodiment of the invention. This embodiment is a modification of that shown in FIG. 5 and all like elements were given the same reference numerals. The difference between the two embodiments lies in that assembly 90 has a piercing member 92 and in that shoulders 94 in this embodiment have some flexibility. Consequently, the central portion 96 of member 34 can be pressed slightly towards membrane 42 and the piercing member 92 will then pierce a hole in that membrane. The hole will be sealed at rest and will open when pressure is applied between the two sides of the membrane.

As will be appreciated, piercing member 92 can have a lumen allowing liquid flow therethrough. Alternatively, liquid can be permitted to flow through the space 98 surrounding the piercing member.

Figure 10:
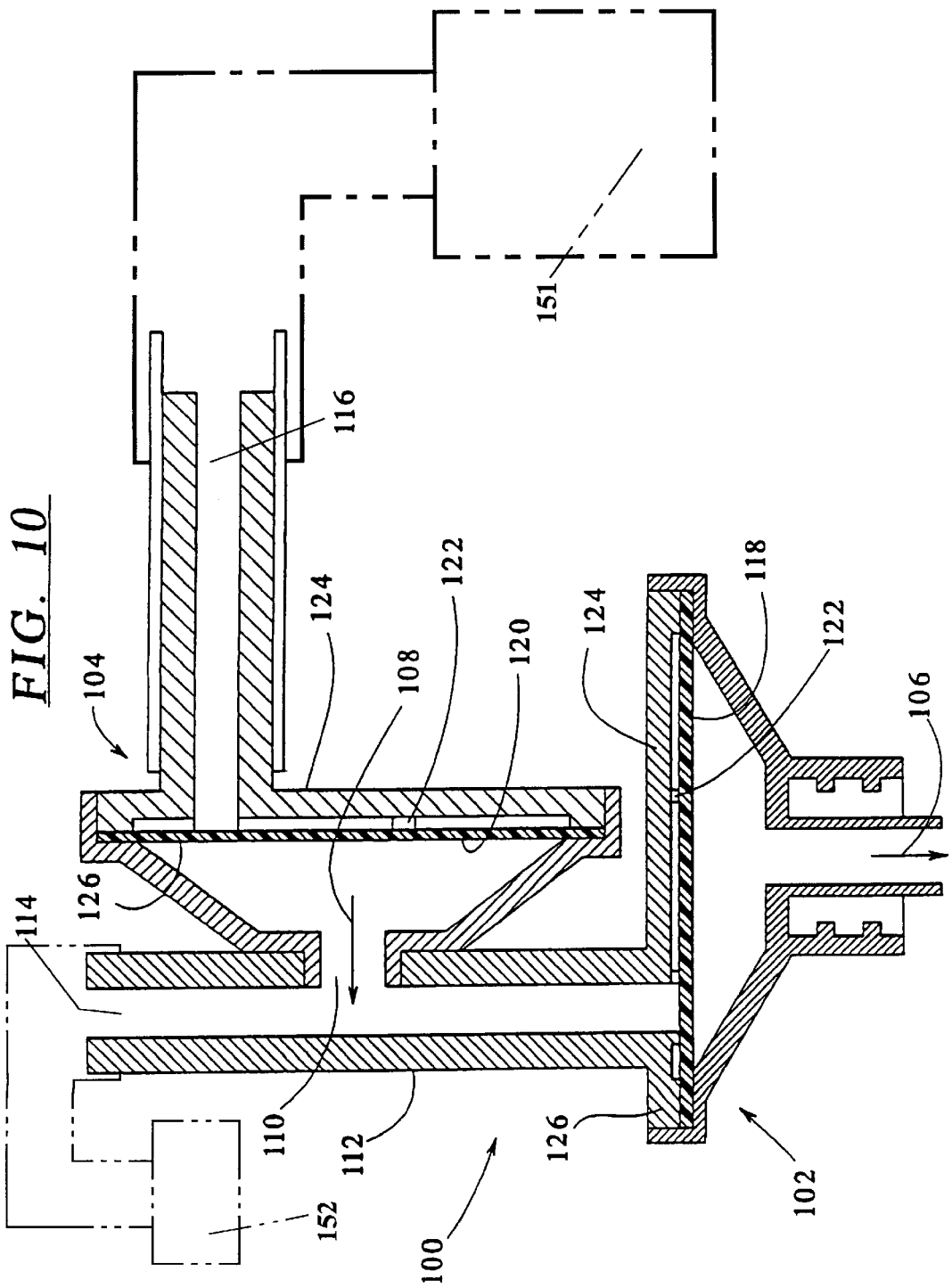
FIG. 10 is a longitudinal cross-section through a valve assembly in accordance with still another embodiment of the present invention constituting a two-way valve.

Attention is now directed to FIG. 10 of the drawings showing a two-way valve generally designated 100. The two-way valve is constructed of two valves 102 and 104, which in the specific embodiment are similar to the valve illustrated in FIG. 6 as hereinabove described.

The first valve 102 is a one-way valve, permitting flow only in the direction of the arrow 106 while the second valve 104 is a one-way valve permitting flow only in the direction of arrow 108. A fluid outlet 110 of the second valve 104 is attached to a fluid inlet tube 112 of the first valve 102, the inlet tube 112 having a free end 114 while valve 104 comprises a fluid inlet 115.

The arrangement is such that the two-way valve 100 has three operative positions. In a first position, fluid is admitted through both the free end 114 and the inlet 116, and as explained in connection with the embodiment of FIG. 6 above, when the liquid pressure exceeds a certain threshold, the membrane 118 of the first valve 102 deforms allowing fluid flow through a pre-existing hole in the membrane (not seen) and via outlet 106.

In a second operative position, fluid is admitted only through the free end 114 with membrane 120 of the second valve 104 serving as a one-way valve, whereby fluid flow is only through the outlet 106 of the first valve member 102.

The third operative position occurs when fluid is admitted only through the fluid inlet 116 of the second valve 104, whereby fluid flows only through the free end 114, owing to essentially high pressure which is required for deforming the membrane 118.

However, a specific application of the valve assembly of FIG. 10 is for example, in a patient feed system, wherein a feed tube is connected to the outlet of the first valve 102 leading to the patient. A first liquid nutrition container (151) is connected to the inlet 116 of the second valve assembly 104 a second liquid container 152 is connected to the inlet 114 via a pump (not shown as known per se). In a first mode of operation the pump pumps liquid from the second liquid container into the inlet tube 112, whereby the liquid is forced through the first valve assembly 102 but can not pass through the second valve assembly 104. In a second mode of operation the pump works in a reversed direction, whereby a measured amount of liquid from the first liquid container is sucked into the line of leading to the second liquid container and than again the pump reverses its operation whereby said measured amount of liquid is pressurized through the first valve assembly 102 as above explained. In this way liquid from either of two containers, e.g., a nutritive agent and water or rinsing agent may be alternately supplied to a patient.

Also seen in FIG. 10, are projections 122 and an annular projection 126 projection from the rear wall 124 of the valve assemblies, for ensuring that the membranes 118 and 120 do not adhere to the rear wall 124 of the valve assemblies 102 and 104, respectively, and that the resilient membranes do not deform in a reverse direction (i.e., in a direction towards the valve's inlets) for ensuring fluid flow in one direction only.

I claim:

1. A valve assembly for liquid transfer, the valve assembly comprising:
   a housing having a liquid inlet, a liquid outlet, and an intermediate liquid port, said intermediate port having an inlet and an outlet;
   a first perforated support plate located between the outlet of the intermediate liquid port and the liquid outlet;
   a second perforated support plate in the housing located between the inlet and outlet of the intermediate liquid port;
   a first valve member positioned in the housing located between the first perforated support plate and the liquid outlet and adjacent the first support plate, the first valve member comprising a resilient membrane having one or more holes through it, the holes open upon deformation of the resilient membrane at a selected threshold pressure over the resilient membrane to permit liquid flow through the resilient membrane but which otherwise prevents liquid flow, the support plate preventing the resilient membrane from deforming sufficiently towards the liquid inlet for preventing flow to the liquid inlet; and
   a second valve member being positioned between the second perforated support plate and the outlet of the intermediate port and adjacent the second support plate, the second valve member comprising a resilient membrane having one or more holes through it, the holes open upon deformation of the resilient membrane at a selected threshold pressure over the resilient membrane to permit liquid flow through the resilient membrane but which otherwise prevents liquid flow, the second support plate preventing the resilient membrane from deforming sufficiently towards the inlet of the intermediate liquid port for preventing flow to the inlet of the intermediate liquid port; and
   a single pump so constructed and arranged to pump liquid from a first container through the first valve member, upon being reversed, the pump sucks liquid through the second valve member from a second container, and upon being reversed again, the pump pumps liquid through the first valve member.

2. A valve assembly according to claim 1 in which the threshold pressure for any resilient membrane is determined by the thickness and surface area of the resilient membrane and the size of the one or more holes.

3. A patient feed system comprising:
(a) a valve assembly for liquid transfer, the valve assembly comprising:
a housing having a liquid inlet, a liquid outlet, and an intermediate liquid port;
a pair of valve members positioned in the housing, a first valve member being positioned between the outlet of the intermediate liquid port and the liquid outlet, and a second valve member being positioned between the inlet and outlet of the intermediate liquid port, each valve member comprising a resilient membrane having one or more holes through it which open upon deformation of the resilient membrane at a selected threshold pressure over the resilient membrane to permit liquid flow through the resilient membrane but which otherwise prevents liquid flow, each resilient membrane being deformable in a flow direction; and
a pair of perforated support plates positioned in the housing, each perforated support plate being associated with a resilient membrane for preventing the resilient membrane from deforming sufficiently in a flow direction opposite the one flow direction of the resilient membrane for preventing liquid from flowing out of the liquid inlet or into the liquid outlet;
(b) a first liquid nutrition container connected to the liquid inlet;
(c) a second liquid container connected to the intermediate liquid port; and
(d) a luer-type connector located at the liquid outlet for connection to a feed tube; and
(e) a single pump so constructed and arranged to pump liquid from the first container through the first valve member, upon being reversed, the pump sucks liquid through the second valve member from the second container, and upon being reversed again, the pump pumps liquid through the first valve member.

* * * * *